(12) United States Patent
Cybulski et al.

(10) Patent No.: US 7,745,133 B2
(45) Date of Patent: Jun. 29, 2010

(54) DETERMINING A PREDISPOSITION TO CANCER

(75) Inventors: Cezary Cybulski, Przeclaw (PL); Jan Lubinski, Szczecin (PL); Bohdan Gorski, Szczecin (PL); Bartlomiej Gliniewicz, Szczecin (PL); Andrzej Sikorski, Szczecin (PL); Tomasz Huzarski, Szczecin (PL); Tadeusz Debniak, Szczecin (PL); Jacek Gronwald, Koszalin (PL); Tomasz Byrski, Szczecin (PL)

(73) Assignee: Pomeranian Academy of Medicine, Szczecin (PL)

( * ) Notice: Subject to any disclaimer, the term of this patent is extended or adjusted under 35 U.S.C. 154(b) by 104 days.

(21) Appl. No.: 11/999,641

(22) Filed: Dec. 5, 2007

(65) Prior Publication Data

US 2009/0197255 A1  Aug. 6, 2009

Related U.S. Application Data

(62) Division of application No. 10/867,578, filed on Jun. 14, 2004, now Pat. No. 7,319,007.

(60) Provisional application No. 60/478,068, filed on Jun. 12, 2003.

(51) Int. Cl.
*C12Q 1/68* (2006.01)
(52) U.S. Cl. ........................................................ 435/6
(58) Field of Classification Search ........................ None
See application file for complete search history.

(56) References Cited

U.S. PATENT DOCUMENTS 6,458,534 B1  10/2002  Conconnon
7,319,007 B2   1/2008  Cybulski et al.

OTHER PUBLICATIONS

Lucentini et al. (The Scientist (2004) vol. 18).*
Wacholder et al. (J. Natl. Cancer Institute (2004) 96(6):434-442).*
Allen et al. (DDT:Targets (2004) 3(6): 183-190).*
Zondervan et al. (Nature Reviews (2004) vol. 5: 89-99).*
Stumm et al. ("No evidence for deletions of the NBS1 gene in lymphomas" Cancer Genet Cytogenet. Apr. 1, 2001;126(1):60-2).*
Carlomango et al. ("Determination of the frequency of the common 657Del5 Nijmegen breakage syndrome mutation in the German population: no association with risk of breast cancer" Genes Chromosomes Cancer. Aug. 1999;25(4):393-5).*
File History of U.S. Appl. No. 10/867,578, filed Jun. 14, 2004.
Carney, James P., et al., "The hMrell/HRad50 protein complex and Nijmegen breakage syndrome: linkage of double-strand break repair to the cellular DNA damage response", Cell, 93(3), (May 1, 1998), 477-486.
Carpten, J. et al., "Germline mutations in the ribonuclease L gene in families showing linkage with HPC1", Nature Genetics, 30(2), (Feb. 2002), 181-184.

Cybulski, C., et al., "CHEK2 Is a Multiorgan Cancer Susceptibility Gene", Am. J. Hum. Genet. vol. 75, (2004), 1131-1135.
Cybulski, C., et al., "NBS1 is a prostate cancer susceptibility gene", Cancer Research, 64(4), (Feb. 15, 2004), 1215-1219.
Debniak, Tadeusz, "Germline 657del5 mutation in the NBS1 gene in patients with malignant melonama of the skin", Melanoma Research, 13, (2003), 365-370.
Digweed, J., "Human genetic instability syndromes: single gene defects with increased risk of cancer", Toxical Lett. 67(1-3), (Apr. 1993), 259-81.
Dong, Xiangyang, et al., "Mutations in CHEK2 Associated with Prostate Cancer Risk", Am. J. Hum. Genet. vol. 72, (2003), 270-280.
Fan, Zuohen, et al., "Adenovirus-mediated antisense ATM gene transfer sensitizes prostate cancer cells to radiation", Cancer Gene Therapy, vol. 7, (2000), 1307-1314.
Futaki, Makoto, "Chromosomal breakage syndromes and the BRCA1 genome surveillance complex", Trends in Molecular Medicine, 7(12), (Dec. 2001), 560-565.
Gayther, Simon A., et al., "The frequency of germ-line mutations in the breast cancer predisposition genes BRCA1 and BRCA2 in familial prostate cancer. The Cancer Research Campaign/British Prostate Group United Kingdom Familial Prostate Cancer Study Collaborators", Cancer Research, 60 (16), (Aug. 15, 2000), 4513-4518.
Gorski, Bohdan, et al., "Germline 657del5 Mutation in the NBS1 Gene in Breast Cancer Patients", Int. J. Cancer, 106, (2003), 379-381.
Koivisto, Pasi A., et al., "Amplification of the Androgen Receptor Gene is Associated with P53 Mutation in Hormone-Refractory Recurrent Prostate Cancer", Journal of Pathology, vol. 187, (1999), 237-241.
Lichtenstein, Paul, et al., "Environmental and Heritable Factors in the Causation of Cancer", The New England Journal of Medicine, 343(2), (Jul. 13, 2000), 78-85.
Matsuura, Shinya, et al., "Positional cloning of the gene for Nijmegen breakage syndrome", Nature Genetics, 19 (Jun. 1998), 179-181.
Plisiecka-Halasa, J., "Nijmegen breakage syndrome gene (NBS1) alterations and its protein (nibrin) expression in human ovarian tumours", Ann. Hum. Genet., vol. 66, (2002), 353-359.
Rebbeck, Timothy R., et al., "Association of HPC2/ELAC2 Genotypes and Prostate Cancer", Am. J. Hum. Genet. vol. 67, (2000), 1014-1019.
Seemanova, E., "An increased risk for malignant neoplasms in heterozygotes for a syndrome of microcephaly, normal intelligence, growth retardation, remarkable facies, immunodeficiency and chromosomal instability", Mutation Research, 238, (1990), 321-324.
Steffen, J. et al., "Frequency of the heterozygous germline NBS1 mutation 657del5 in cancer patients from Poland", Casopis Lekaru Ceskych, 141(8), International Workshop on Nijmegen Breakage Syndrome, Prague, Czech Republic, (2002), VII-VIII.

(Continued)

*Primary Examiner*—Christopher M. Babic
(74) *Attorney, Agent, or Firm*—Gary J. Gershik; Cooper & Dunham LLP (57) ABSTRACT

The present invention relates to methods and kits for determining a predisposition for developing cancer, e.g., prostate and/or breast cancer, due to a germline mutation of a NBS1 gene. The present invention also relates to surveillance protocols for developing cancer, e.g., prostate and/or breast cancer, due to germline mutation of a NBS1 gene.

12 Claims, 2 Drawing Sheets

OTHER PUBLICATIONS

Steffen, Jan, et al., "Increased Cancer risk of Heterozygotes with NBS1 Germline Mutation in Poland", Int. J. Cancer., vol. 111 (2004), 67-71.

Tavtigian, Sean V., et al., "A candidate prostate cancer susceptibility gene at chromosome 17p", Nature Genetics, 27, (Feb. 2001), 172-180.

Van der Burgt, Ineke, et al., "Nijmegen breakage syndrome", J. Med. Genet. 33(2), (Feb. 1996), 153-156.

Varon, Raymonda, "Clinical ascertainment of Nijmegen breakage syndrome (NBS) and prevalence of the major mutation, 657del5 in three Slav populations", European Journal of Human Genetics, vol. 8, (2000), 900-902.

Varon, Raymonda, "Mutations in the Nijmegen Breakage Syndrome Gene (NBS1) in Childhood Acute Lynphoblastic Leukemia (ALL)", Cancer Research, vol. 61, (May 1, 2001), 3570-3572.

Varon, Ramonda, "Nibrin, a Novel DNA Double-strand Break Repair Protein, Is Mutated in Nijmegen Breakage Syndrom", Cell, vol. 93, (May 1, 1998), 467-476.

Voelkel-Johnson, Christina, et al., "Genomic instability-based transgenic models of prostate cancer", Carcinogenesis, 21(8), (2000), 1623-1627.

Wang, Liang, et al., "Role of HPC/ELAC2 in Hereditary Prostate Cancer1", Cancer Research, vol. 61, (Sep. 1, 2001), 6494-6499.

Xu, J., et al., "Evaluation of linkage and association of HPC2/ELAC2 in patients with familial or specific prostate cancer", Am. J. Hum Genet., (68(4), (Apr. 2001), 901-11.

Xu, Jiangeng, et al., "Genomewide Screen and Identification of Gene-Gene Interactions for Asthma-Susceptibility Loci In Three U.S. Populations: Collaborative Study on the Genetics of Asthma", American Journal of Human Genetics, 68, (Jun. 2001), 1437-1446.

Carlomango et al., "Determination of the frequency of the common 657Del5 Nijmegen breakage syndrome mutation in the German population: no association with risk of breast cancer", Genes Chromosomes Cancer, (1999) 25(4):393-5.

Stumm et al., "No evidence for deletions of the NBS1 gene in lymphomas", Cancer Genet Cytogenet (2001) 126(1):60-2.

* cited by examiner

DETERMINING A PREDISPOSITION TO CANCER

CLAIM OF PRIORITY

This application is a divisional of U.S. Ser. No. 10/867,578, filed Jun. 14, 2004, now U.S. Pat. No. 7,319,007, issued Jan. 15, 2008, claiming priority of U.S. Provisional Patent Application Ser. No. 60/478,068, filed Jun. 12, 2003, the contents of all of which are hereby incorporated by reference into this application.

FIELD OF THE INVENTION

The present invention relates to methods and kits for determining a subject's predisposition for developing cancer, e.g., prostate or breast cancer.

BACKGROUND OF THE INVENTION

Prostate cancer is a leading cause of morbidity and mortality in men. Outside of the context of a family history, relatively little is known about the genetic determinants that cause prostate cancer. Epidemiological studies suggest that 5-10% of all prostate cancers are attributable to high penetrance susceptibility genes. The strongest evidence for the role of inherited genetic factors in development of prostate cancer comes from a Scandinavian study on twins that suggested that as many as 42% of prostate cancer risk could be explained by an inherited predisposition (Lichtenstein et al., 2000). Evidence also points to a complex genetic basis of prostate cancer, involving multiple susceptibility genes and variable phenotypic expression. Different chromosomal loci have been linked to prostate cancer including: HPC1, HPC2, PCAP, CAPB, HPCX, 20q13, 16q23. However, no major prostate susceptibility genes have so far been identified. Only two studies have shown any success cloning candidate susceptibility genes from these regions: HPC1 (MIM 601518) and HPC2/ELAC2 (MIM 605367) (Tavtigian et al., 2001; Carpten et al., 2002). However, other studies suggested a limited role for those genes in hereditary prostate canter (Wang et al., 2001; Xu et al., 2001; and Rebbeck et al., 2000).

Breast cancer is also a common disease. Each year, approximately 200,000 women in the United States alone are diagnosed with breast cancer, and one in nine American women will develop breast cancer in her lifetime. Hereditary breast cancer is caused by mutated genes passed from parents to their children. Estimates of the incidence of hereditary breast cancer range from between 5 to 10 percent to as many as 27 percent of all breast cancers.

In 1994, the first gene associated with breast cancer, BRCA1 (BReast CAncer1) was identified on chromosome 17. A year later, a second gene associated with breast cancer, BRCA2, was discovered on chromosome 13. When individuals carry a mutated form of either BRCA1 or BRCA2, they have an increased risk of developing breast at some point in their lives. Not all hereditary breast cancers are caused by BRCA1 and BRCA2. In fact, researchers now believe that at least half of hereditary breast cancers are not linked to these genes.

Accordingly, there is a need for the identification of genetic markers that indicate a predisposition for developing cancer, e.g., prostate cancer and/or breast cancer, that can be used to identify subjects that have an increased susceptibility for developing cancer, i.e., they are predisposed to develop cancer.

SUMMARY OF CERTAIN EMBODIMENTS OF THE INVENTION

It has been established that the NBS1 gene has a role in pathogenesis of prostate cancer and breast cancer, e.g., invasive breast carcinoma of the lobular subtype. Specifically, subjects having a mutation in at least one allele of the NBS1 gene have an increased susceptibility for developing cancer, i.e., they are predisposed to develop cancer. Accordingly, the present invention provides methods and kits for detecting predispositions to cancer in subjects and identifying such subjects for additional diagnostic screening, e.g., early cancer screening.

The present invention provides a method for detecting a predisposition to prostate cancer in a subject, including detecting in a biological sample from the subject an alteration in the sequence of a NBS1 gene, wherein the alteration is indicative of a predisposition to prostate cancer.

The present invention also provides a method for detecting a predisposition to lobular invasive subtype of breast cancer in a subject, including detecting in a biological sample from the subject an alteration in the sequence of a NBS1 gene, wherein the alteration is indicative of a predisposition to breast cancer. In some embodiments of the invention, the breast cancer is invasive breast cancer of the lobular subtype.

The present invention further provides a diagnostic kit for identifying a predisposition to breast cancer or prostate cancer in a subject, including packaging material and at least two different polynucleotides capable of amplifying at least a region of a NBS1 gene.

The present invention further provides a method for diagnosing breast cancer or prostate cancer in a subject, including detecting in a biological sample from the subject an alteration in the sequence of a NBS1 gene, wherein the alteration is indicative of a predisposition to cancer.

DETAILED DESCRIPTION OF THE INVENTION

It has been established that the NBS1 gene has a role in pathogenesis of prostate cancer and lobular invasive breast cancer. Specifically, subjects having a mutation in at least one allele of a NBS1 gene have an increased susceptibility for developing prostate or breast cancer.

Accordingly, the present invention provides a method for detecting a predisposition to prostate cancer in a subject, including detecting in a biological sample from the subject an alteration in the sequence of a NBS1 gene, wherein the alteration is indicative of a predisposition to prostate cancer.

The present invention also provides a method for detecting a predisposition to lobular invasive breast cancer in a subject, including detecting in a biological sample from the subject an alteration in the sequence of a NBS1 gene, wherein the alteration is indicative of a predisposition to breast cancer.

The present invention also provides a method for diagnosing breast cancer or prostate cancer in a subject, including detecting in a biological sample from the subject an alteration in the sequence of a NBS1 gene, wherein the alteration is indicative of a predisposition to cancer. If such an alteration is detected, additional methods, e.g., mammagraphy, may be performed to diagnose the subject.

The subject may be a human, e.g., of Slavic origin. For example, the subject may be: East Slavic, e.g., Belarusian, Russian, and/or Ukrainian; South Slavic, e.g., Bulgarian, Macedonian, Serbo-Croatian, Slovene; and/or West Slavic, e.g., Czech, Polish, Slovak, and/or Sorbian.

In the invention, the alteration can be a germline alteration, e.g., 657del5. The alteration may be present in the sequence of a single allele of the NBS1 gene, or the alteration may be present in the sequence of more than one allele, e.g., two alleles, of the NBS1 gene. The alteration may be a mutation in the NBS1 gene, e.g., a mutation caused an insertion into the gene, a deletion of a portion of the gene, or a change of nucleotide(s) in the gene. In some embodiments, the alteration in the gene affects, e.g. inhibits, the production of protein encoded by the NBS1 gene. The alteration may result in the production of a different, e.g. a truncated, protein in comparison to the protein that would be produced by the NBS1 gene. Such a protein may not possess the functional capabilities possessed by the protein encoded by the NBS1 gene.

The alteration can be detected by any technique capable of detecting the NBS1 alteration, including but not limited to microchip ASO PCR, SSCP, direct sequencing, ASA-, or RFLP-PCR. The predisposition may be an inherited predisposition. In some embodiments, the biological sample may be a tissue sample such as blood. In some embodiments of the invention, the breast cancer is invasive breast cancer of the lobular subtype.

The present invention further provides a diagnostic kit for identifying a predisposition to breast cancer or prostate cancer in a subject, including packaging material and at least two different polynucleotides capable of amplifying at least a region of a NBS1 gene. In some embodiments of the invention, the amplified region includes mutation 657del5. In some embodiments of the invention, the kit may contain polynucleotides Nbsex6f, Nbsex6r and Nbsdel5. The kit may also contain instructions, e.g., instructions for using the kit to identify a predisposition to breast cancer or prostate cancer in a subject.

The methods and kits provided herein are useful for determining a predisposition for cancers such as prostate and lobular invasive breast cancer, and they are also useful for diagnosing cancers such as prostate and breast cancers, e.g., at earliest clinical stages.

An alteration in the NBS1 gene, e.g., the 657del5 alteration, may be detected by any assay that is capable of detecting an alteration, e.g., using nucleotide extension assays, sequencing assays, hybridization assays, and/or amplification assays. An alteration may be detected by performing assays on any form of DNA or RNA obtained from the subject. For example, the art worker could identify an alteration using allele-specific oligonucleotide-PCR (ASO PCR), assays to detect single-stranded conformation polymorphism (SSCP), direct sequencing, allele-specific amplification (ASA), allele-specific hybridization (ASH), and/or restriction fragment length polymorphism analysis after PCR amplification (RFLP-PCR). Hybridization conditions may be performed under various conditions selected by the art worker. Some examples are described hereinbelow.

"Stringent hybridization conditions" and "stringent hybridization wash conditions" in the context of polynucleotide hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of polynucleotides is found in Tijssen, *Laboratory Techniques in Biochemistry and Molecular Biology Hybridization with Nucleic Acid Probes*, part I chapter 2 "Overview of principles of hybridization and the strategy of polynucleotide probe assays" Elsevier, N.Y. (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Molecular Cloning: A Laboratory Manual; Sambrook et al., 3rd Ed., Cold Spring Harbor Laboratory Press, (2001) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Polynucleotides that do not hybridize to each other under stringent conditions are still substantially identical if the proteins that they encode are substantially identical. This occurs, e.g., when a copy of a polynucleotide is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Several polynucleotides are described here that are useful for detecting the alterations, and the art worker in would be able to design other polynucleotides that would be useful in detecting the alteration. Thus, the present invention also provides polynucleotides comprising, consisting essentially of, or consisting of any of SEQ ID NOs 2-8.

Human tumors are often associated with genomic instability, and the DNA damage signaling pathway has a crucial role in maintaining of the integrity of genome in response to DNA damaging factors. This pathway may play an important role in pathogenesis of cancer. DNA damage signaling is disrupted by mutations causing human chromosomal breakage syndromes such as Nijmegen syndrome (NBS), Bloom syndrome, Fanconi anaemia and ataxia telangiectasia (AT), which are characterized by spontaneous chromosomal instability, immunodeficiency, and a predisposition to cancer (Digweed, 1993; and Futaki et al., 2001). The Nijmegen breakage syndrome gene NBS1 was mapped to chromosome 8q21 and cloned (see Varon et al., 1998; U.S. Pat. No. 6,458,534; and Genbank, Accession AB013139). The product of the NBS1 gene, nibrin (also referred to as p95) is an integral component of the hMRE11/hRAD50/NBS1 nuclease complex, which is a part of BRCA1-associated genome surveillance complex (BASC) responsible for DNA damage repair (Futaki et al., 2001). A truncating 5 bp deletion in exon 6 of the NBS1 gene was detected in the vast majority of NBS patients. Most of the reported NBS patients are of the Slavic origin and carry a major 657del5 founder mutation. This mutation is present with an unexpectedly high carrier frequency in Poland, Ukraine, and the Czech Republic (Varon et al., 2000). The role of NBS1 gene in prostate and lobular invasive breast cancer development has not yet been investigated.

A fragment of the genomic sequence of NBS1 gene, including exon 6, is depicted below as SEQ ID NO:1. The sequence of exon 6 is shown in bold, and the 657del5 mutation is shown in italics. (also, see Genbank, Accession Number AB013139; Matsuura et al., 1998))

```
17941  cagataaaat tcttacttaa aaaaaatact ataaaggtat
       tatggaaatt atgccttttg 18001  agtgtcagat agtcactccg tttacaattt aatagcaaac
       atagtagtat ataattagaa 18061  tatactttaa ttattttac agttttacc cacctcttga
       tgaaccatct attggaagta 18121  aaatgttga tctgtcagga cggcaggaaa gaaaacaaat
       cttcaaaggg aaaacattta 18181  tattttgaa tgccaaacag gtaattatgt tataagctaa
       atttttcctaa agaatacatt 18241  acaaactagg atacattatt aactcttatc agtagttgtt
       aacgtatttc attttgggat
```

-continued

```
18301  tttgtgtaaa agtgtgaagt agaataaaaa aaccccaggc
       accagacctg cccagtgatc 18361  atggctgtga ttacgggggtt tcttaaaatc tgtgataact
       ggcctattca taaatatgca 18421  agtgagaagg acaggaaact tagttttaac ttctttagtt
       agtaagctaa acctctttag
```

As described herein, NBS1 appears to act as a classical tumor suppressor gene because biallelic NBS1 inactivation was observed in most tumors. However, some degree of haploinsufficiency and possible dominant-negative effect of NBS1 mutations are not ruled out because it has not been established that NBS1 heterozygous cells have impaired DNA repair capacity. The NBS1 founder allele is predicted to result in a truncated protein of 219 of 754 amino acids (p26). p26 lacks crucial domain necessary for MRE11 interaction. It is not known whether this mutant protein possesses any residual activity or exerts a dominant-negative effect. However, the 657del5 allele also creates an aberrant translation initiation site, which generates a partially functional variant of the NBS1 protein (p70). p70 contains the MRE11 binding domain but does not confer full function within the MRE11 complex. In light of this, it is possible that p70 may produce a dominant-negative effect.

The methods and kits of the invention can be used to determine a subject's predisposition invasive lobular breast carcinoma (ILC).

Portions of Applicants' invention have been published as Cybulski et al., 2004.

The invention will now be illustrated by the following non-limiting Examples.

Example 1

The correlation between a germline alteration in the sequence of the NBS1 gene sequence and inherited predisposition to prostate cancer and breast cancer on example of analysis of 657 del5 founder mutation in the NBS1 gene was calculated.

Patients

A. The Association Between 657del5 and Prostate Cancer

Cases suspected of prostate cancer were admitted to Clinics of Urology in Szczecin. Criteria for suspicion of prostate cancer were elevated PSA level above 4.0 ng/ml or abnormal findings in per recum examination. Prostate cancer was diagnosed in the Clinics on the basis of USG-guided DRECUT biopsy performed in the suspected cases. Biopsy tissues, stained using standard procedures, were evaluated by pathologists in Department of Genetics and Pathology in Szczecin, and final diagnosis was confirmed.

All 359 men diagnosed with prostate cancer at the University Hospital in Szczecin, Poland between 1999 and 2002 were invited to participate in this study. Of these, 340 (95%) agreed to participate. All cases were recruited within six months of the date of diagnosis. Family histories of cancer were obtained from each subject. Thirty-five patients (10.3%) had one or more first- or second-degree relative with prostate cancer (familial cases). A second set of 21 familial cases of prostate cancer from men who were referred for evaluation at the Hereditary Cancer Center by family doctors or urologists because of familial aggregation of prostate cancers were also included. In total, there were 56 familial cases and 305 non-familial cases. The familial cases from the incident sample contained, on average, 2.1 cases of prostate cancer (mean age of onset 67.3 years) and the familial cases from the Hereditary Cancer Center sample contained 2.6 cases of prostate cancer (mean age of onset 63.3 years). There were 1500 unaffected controls. One thousand controls were selected at random from the computerized patient lists of three family practices in Szczecin (508 females and 492 males; age range 26 to 89 years). In addition, a second control group of 500 unselected newborns from Szczecin for whom a sample of umbilical cord blood samples was available were included.

B. The Association Between 657del5 and Breast Cancer of Lobular Subtype

The study group included 2012 unselected women with breast cancer. Breast cancer cases were recruited from 8 hospitals throughout Poland (see Table 1). Patients were consecutively ascertained from the pathology departments of the treating hospitals. Only primary invasive breast cancer cases were included (cases of DCIS and LCIS were excluded). Patients were collected between 2002 and 2003. Two thousand controls from the general population were used for the study of the association between the NBS1 founder allele and breast cancer (1000 unselected adults from Szczecin and 1000 newborn children in 2003 form six hospitals throughout Poland).

TABLE 1

Prevalence of mutant NBS1 founder allele among breast cancer patients in eight regions of Poland

| City | Number of subjects | NBS1 657del5 |
|---|---|---|
| Szczecin | 511 | 5 |
| Bielsko Biala | 172 | 2 |
| Opole | 480 | 5 |
| Poznań | 258 | 1 |
| Kraków | 251 | 2 |
| Koszalin | 110 | 1 |
| Lublin | 179 | 1 |
| Bydgoszcz | 51 | 0 |
| Total | 2012 | 17 |

Methods

ASO-PCR and sequencing was used for detection of the NBS1 founder mutation in DNA isolated from peripheral blood leukocytes. To analyze if the NBS1 wild type allele is lost in prostate cancer, LOH analysis in microdissected tumors from NBS1 mutation carriers was performed. To LOH analysis, 9 of 12 prostate cancer tumors in which it was possible to microdissect fields of tumor cells were qualified. LOH was carried out using markers adjacent to NBS1 gene: D8S88 and D8S1811 as described in Górski et al., 2003 and Dębniak et al., 2003. NBS1 exon6-specific primers were fluorescently labeled.

5 ml of peripheral blood was obtained from cancer patients and mixed with 100 µl 1M EDTA, then was centrifuged in 50 ml polypropylene tubes by 10 minutes at 3000 g in 4° C. Serum in the upper faze was removed, and the pellet containing cells was mixed with 45 ml buffer 2× (0.1M $NH_4Cl$, 0.25M $KHCO_3$, 1 mM EDTA) and was left for 15 minutes in 4° C. Then mixture was centrifuged at 3000 g for 10 minutes in 4° C. Supernatant was removed after centrifugation. The remaining pellet with leukocytes was suspended in 2× buffer and centrifuged 10 minutes at 3000 g in 4° C. This purification of leukocytes in 2× buffer and centrifugation was repeated three times until pure leukocyte pellet was obtained. The leukocytes were then mixed with 3 ml digestion buffer (5 mM NaCl, 25 mM $MgCl_2$, 1 mM EDTA; pH 8.0) with 200 µl 10% SDS and 500 µg Proteinase K. Digestion was carried out 24 h in 37° C.

DNA was purified using phenol/chloroform. In brief, digestion products were mixed with 3 ml phenol buffered 0.5M Tris HCl (pH 8.4), and then 3 ml chloroform and isoamyl alcohol mixture (mixed in proportion 1:25 vol/vol). The mixture was agitated for about 1 minute and centrifuged for 10 minutes at 8000 g in 20° C. After centrifugation, the upper faze was placed in a new tube and mixed with an equal volume of chloroform and thereafter centrifuged for 10 minutes at 8000 g. The above-described purification with chloroform was repeated 3 times until the protein ring in interfaze had disappeared.

The purified water faze containing DNA was mixed with 5M NaCl in proportion 10:1 (vol/vol) and 96% ethanol in the proportion of water faze with NaCl to ethanol 1:10 (vol/vol). The mixture was left overnight in 20° C. The resultant DNA pellet was placed in a new tube and purified with 70% ethanol, centrifuged at 3000 g for 5 minutes, and ethanol was poured out. The purified DNA pellet was then dried in an open tube for 30 minutes at 37° C. DNA was resuspended in 400 µl TE buffer (25 mM Tris HCl, 1 mM EDTA; pH 8.4) and was stored at 4° C. until use.

Allele Specific-PCR (ASO-PCR)

ASO-PCR reaction was carried out in DNA ThermalCycler 9600 (Perkin Elmer) in a volume of 25 µl, including: 1 µl (50 ng) genomic DNA, 4 µmol Nbsex6f primer, 6 pmol Nbsex6r primer, 10 pmol Nbsdel5 primer, 2.5 µl PCR buffer (1100 mM Tris-HCl, 500 mM KCL, 15 mM $MgCl_2$, 1 mg/ml gelatin; pH 8.6), 200 µM each dATP, dCTP, dGTP idTTP and 1 U Taq DNA polymerase. In each reaction 2 positive controls (controls with DNA from NBS1 heterozygote and NBS1 homozygote) and 2 negative controls (control DNA from NBS1 mutation negative patient and control without DNA) were used.

ASO-PCR Conditions:

a) Initial denaturation - 95° C. 5 minutes
b) 11 cycles, each of:
   denaturation - 94° C. 30 s
   primer annealing - 62 to 56° C. 30 s *
   primer elongation - 72° C. 30 s
c) 30 cycles, each of:
   denaturation - 94° C. 30 s
   primer annealing - 56° C. 30 s
   primer elongation - 72° C. 30 s

* during first 11 cycles primer annealing temperature was lowered by 0.6° C. in each cycle beginning from 62° C. in the first one and ending to 56° C. in the 11$^{th}$ cycle (in detail: 1$^{st}$ cycle - 62° C., 2$^{nd}$ - 61.4° C., 3$^{rd}$ - 60.8° C., 4$^{th}$ - 60.2° C., 5$^{th}$ - 59.6° C., 6$^{th}$ - 59° C., 7$^{th}$ - 58.4° C., 8$^{th}$ - 57.8° C., 9$^{th}$ - 57.2° C., 10$^{th}$ - 56.6° C., 11$^{th}$ - 56° C.)

Sequence of Primers Used in ASO-PCR:

Nbsex6f:  5' CACCTCTTGATGAACCATCT 3'   (SEQ ID NO:2)

Nbsex6r:  5' CGTTAACAACTACTGATAAGAG 3' (SEQ ID NO:3)

Nbsdel5:  5' GGACGGCAGGAAAGAAATCTT 3'  (SEQ ID NO:4)
          (657del5 specific primer)

5 µl of PCR products was mixed with 10 µl loading buffer and electrophoresed in agarose gel (1.5% agarose gel (SeaKem FMC), 1× bufor TBE, 25 µg/ml bromku etydyny) at 6V/cm for 30 minutes. Separated products were visualized in UV light. All cases in which additional shorter PCR products were observed were sequenced in order to confirm the presence of NBS1 founder mutation.

Sequencing Template PCR

Exon 6 of the NBS1 gene was amplified with Nbsex6f and Nbsex6r primers in conditions as described in ASO-PCR without primer Nbsdel5.

Purification of PCR Products

Products of amplification of exon 6 were pippeted into a Microcon-100 sample reservoir (Amicon) and placed into vial. 400 μl dH$_2$O was added to the reservoir which was centrifuged at 1850 g for 15 minutes. After centrifugation, the sample reservoir was inserted into a new vial, filled with 400 μl dH$_2$O and centrifuged at 1850 g for 15 minutes. The latter was repeated 3-times. The sample reservoir was placed upside down in a new vial and then spun for 3 minutes at 9000 g. All spins were carried out at 25° C. About 5 μl of purified PCR product was in the vial, and it was diluted in 20 μl dH$_2$O.

Sequencing PCR

Asymmetric sequencing PCR was performed in GeneAmp PCR System 9600 thermocycler (Perkin Elmer) in a volume of 20 μl containing: 1 pmol Nbsex16f primer, 4 μl purified PCR product, 8 μl BigDye Terminator Ready Reaction Kit v3.0 (Applied Biosystems). In addition, a sequencing reaction with Nbsdel6r primer was carried to confirm results with the forward primer.

Sequencing Conditions:

---

Initial denaturation - 96° C. 30 s
30 cycles, each of:

denaturation - 94° C. 30 s
primer annealing - 56° C. 30 s
primer elongation - 72° C. 30 s

---

20 μl of the sequencing product was placed into a 0.5 ml Eppendorf tube, and 60 μl 96% ethanol and 2 μl 3M sodium citrate (pH 4.6) were added. Probes were centrifuged for 20 minutes at 3 000 g in 25° C. Then supernatant was removed, and 200 μl 70% ethanol was added to purify the pellet. After a 5 minute centrifugation at 3000 g at 25° C., the supernatant was removed. The pellet was dried in an Eppendorf Concentrator 5301 for 20-30 min and then resuspended in 4 μl of loading buffer (150 μl deionized formamide, 50 μl 50 mM EDTA, 0.05% Dextran Blue). Samples were denaturated for 4 minutes at 94° C., put on ice, and loaded onto denaturating polyacrylamide gel (4% 19:1 polyacrylamide gel, 1×TBE, 6M urea). Electrophoresis was carried out in ABI PRISM 377 DNA Sequencer (Applied Biosystems). Data collection and analysis was performed using ABI PRISM 377 Collection Software and Sequencing Analysis Software Version 3.0 (Applied Biosystems).

Example 2

Loss of Heterozygosity Analysis (LOH) in Prostate and Breast Cancers

To analyze if NBS1 wild type allele is lost in prostate cancer and/or breast cancer, LOH analysis in microdissected tumors from NBS1 mutation carriers was carried out on 9 prostate cancer and 5 breast cancer tumors. LOH was carried out using markers adjacent to NBS1 gene: D8S88, D8S1811. Fluorescently labeled NBS1 exon6-specific primers were used (Cybulski et al., 2004).

Microdissection and DNA Isolation

Five micron sections of formalin-fixed, paraffin embedded tissues were cut onto slides. From each patient, tissues were sectioned onto 6 slides. One was hematoxylin/eosin stained. The remaining were used for microdissection. Sections were deparaffinized in two changes of xylene for 5 minutes. Sections were hydrated through a series of graded alcohols (in 96% ethanol (2-times), 70% ethanol and dH$_2$O in each for 5 minutes). The slides were then stained in hematoxilin. Using a light microscope, the homogenous fields of cancer cells were chosen in HE stained sections. Those fields were carefully microdissected using a needle from slides stained with hematoxylin only under light microscope, avoiding contamination with nonmalignant cells. Microdissected tissues were put into 1.5 ml Eppendorf tubes. In parallel, normal tissues were cut out from the same slides and put into separate tubes.

Microdissected tissues were then digested in 1 ml digestion buffer (50 mM TrisHCl, 1 mM CaCl$_2$, pH 8.0) with 20 μl 10% SDS and 500 μg proteinase K. In each series negative controls without tissue were used. Enzymatic digestion was carried out at 55° C. for 2 weeks. At the $3^{rd}$ and $6^{th}$ day of digestion, an additional 100 μg proteinase K was added. After digestion, the proteinase was heat inactivated at 96° C. for 10 minutes. 500 μl of digestion product was purified in Microcon-100 tubes (Amicon) according to procedure described herein. After purification, about 5 μl of solution containing DNA was diluted in 50 μl dH$_2$O.

LOH Analysis

LOH analysis was performed in 3 PCR reactions with fluorescent primers:

1) PCR1 with primers D8S88f: 5' TCCAGCAGAGAAAGGGTTAT 3' (SEQ ID NO:5); D8S88r: 5' GGCAAAGAGAACTCATCAGA 3' (SEQ ID NO:6);
2) PCR2 with primers D8S1811f: 5' CCCACCCCCAAAATGC 3' (SEQ ID NO:7); D8S1811r: 5' GGGTTTAGGGAAGTGCAGAA 3' (SEQ ID NO:8); and
3) PCR3 with primers Nbsex6f and Nbsex6r flanking NBS1 exon 6 containing 657del5.

PCR reaction was carried out in DNA ThermalCycler 9600 (Perkin Elmer) in a volume of 25 μl, which included: 4 μl DNA isolated from tissues, 2.5 μl PCR buffer (100 mM TrisHCl, 500 mM KCL, 15 mM MgCl$_2$, 1 mg/ml gelatin; pH 8.6), 200 μM each dATP, dCTP, dGTP i dTTP, 1 U Taq DNA Polymerase and 10 μg bovine serum albumin (BSA—Fermentas). PCR1 mixture also included 5 pmol D8S88f and D8S88r primers. PCR2 mixture also included 5 pmol D8S1811f and D8S1811r primers. PCR3 mixture also included 5 pmol Nbsex6f and Nbsex6r primers. In each PCR reaction, positive and negative controls were used.

PCR Conditions:

--- c) Initial denaturation - 95° C. 5 minutes
d) 42 cycles, each of:
    denaturation - 94° C. 30 s
    primer annealing - 56° C. 30 s
    primer elongation - 72° C. 30 s

---

One μl of PCR product was diluted in 10 μl loading buffer (150 μl formamid, 50 μl 50 mM EDTA, 0.05% Dextran Blue). After denaturation for 4 minutes at 94° C., samples were put into ice and loaded onto denaturating polyacrylamide gel (4% 19:1 polyacrylamide gel, 1×TBE, 6M urea). Electrophoresis was carried our in an ABI PRISM 377 DNA Sequencer (Applied Biosystems). Data collection and analysis was performed using ABI PRISM 377 Collection Software and GenScan Analysis Software Version 3.0 (Applied Biosystems). A signal reduction in one allele of at least 75% was taken is the threshold of recognition for LOH.

Statistical Analysis was Performed Using Chi-square Test.

Results

The NBS1 mutation was present in nine of 340 unselected prostate cancer cases (2.6%), compared to only nine of 1500 (0.6%) control individuals from the general population (odds ratio 4.5; 95% CI 1.7 to 11.5; p=0.002). The 657del5 germline mutation was present in five of the 56 (9%) familial cases (odds ratio=16; 95% CI=5.2 to 50; p<0.0001). The segregation of the NBS1 mutant allele with prostate cancer was investigated in four families. The mutation status was established in two affected males from each family. In each family the NBS1 mutation was present in both affected members.

The 657 del5 allele was found in 17 (0.8%) of 2012 consecutive breast cancers, compared to 8 in 2000 controls (odds ratio 1.9; 95% CI=0.8 to 4.2, p=0.17). Paraffin embedded tissues were obtained from 12 breast tumors form NBS1 mutation carriers. The type of these tumors was verified by two pathologists after H&E and immunohistochemical staining. Nine of 12 breast cancers were large cell infiltrating lobular carcinomas (see Table 2). H&E sections were available from 491 out of 2012 studied cases. All of them were from one center: a regional oncology hospital in Szczecin. Two pathologist established the breast cancer subtype in all 491 cases. Lobular carcinomas were diagnosed in 53 of the 491 breast consecutive cancers. Of these 53 breast cancer patients, NBS1 mutations were detected in 4 (7.5%) cases (OR 18.4, 95% CI 5.5-62, p<0.0001). Thus, the NBS1 mutation is associated with large cell infiltrating lobular carcinoma or the breast.

tion prevalence of 1 in 167, the gene is estimated to be responsible for about 2% of prostate cancers in this country. Statistically significant excess of the NBS1 founder allele in women with unselected breast cancer was not observed. However, the 657 del5 was associated with increased risk of invasive lobular breast carcinoma (OR 18.4, p<0.0001). Given the geographic distribution of reported clinical cases of the Nijmegen breakage syndrome, the 657del5 mutation is also an important contributor to prostate and lobular breast cancer in patients of Slavic origin from other countries (the 657del5 allele is responsible for all cases of the Nijmegen breakage syndrome in all Slavic populations reported to date).

This is the first report exploring the role of NBS1 gene in development of prostate cancer. Statistically significantly more frequent occurrence of NBS1 founder mutation in series of consecutive prostate cancer subjects (odds ratio 4.5; 95% CI 1.7 to 11.5; p=0.002) and familial prostate cancer cases (odds ratio=16; 95% CI=5.2 to 50; p<0.0001) compared to its prevalence in the general population was found. The loss of the wild type NBS1 allele in prostate cancer tumor tissue from 657del5 mutation carriers strongly points at the role of NBS1 mutation in pathogenesis of prostate canter. The 657del5 mutation may contribute to prostate cancer risk not only in the Slavic populations but also in patients of Slavic origin in other countries. The major NBS1 mutation is very common and constitutes 100% of all NBS1 gene changes reported in germline of NBS patients from the Slavic populations. Thus,

TABLE 2

Histopathological data of carriers of 657del5 alteration among woman with breast cancer

| Patient | Age (yr) | First Pathology Diagnosis | Pathology Diagnosis after Re-evaluation of the Slides |
|---|---|---|---|
| 1 | 44 | Infiltrating ductal carcinoma | Infiltrating ductal carcinoma |
| 2 | 56 | Infiltrating lobular carcinoma | Infiltrating lobular carcinoma |
| 3 | 38 | Infiltrating ductal carcinoma | Infiltrating ductal carcinoma |
| 4 | 42 | Infiltrating ductal carcinoma | Infiltrating lobular carcinoma |
| 5 | 47 | Infiltrating lobular carcinoma | Infiltrating lobular carcinoma |
| 6 | 47 | Infiltrating tubular carcinoma | Infiltrating tubular carcinoma |
| 7 | 68 | Infiltrating lobular carcinoma | Infiltrating lobular carcinoma |
| 8 | 46 | Infiltrating lobular carcinoma | Infiltrating lobular carcinoma |
| 9 | 57 | Infiltrating lobular carcinoma | Infiltrating lobular carcinoma |
| 10 | 49 | Infiltrating ductal carcinoma | Infiltrating lobular carcinoma |
| 11 | 46 | Infiltrating lobular carcinoma | Infiltrating lobular carcinoma |
| 12 | 52 | Infiltrating lobular carcinoma | Infiltrating lobular carcinoma |

Loss of the wild type NBS1 allele was observed in 7 of 8 prostate cancers and in 5 of 5 breast cancers. The data on the loss of heterozygosity indicates that NBS1 functions as a classical tumor suppressor gene. Clinically, the Nijmegen breakage syndrome is a recessive genetic condition. The heterozygote state may not be deleterious at the cellular level but, loss of heterozygosity renders cells hemizygous for the mutant allele. Cultured cells homozygous for the NBS1 mutation are prone to chromosomal aberrations.

Figure 1A:
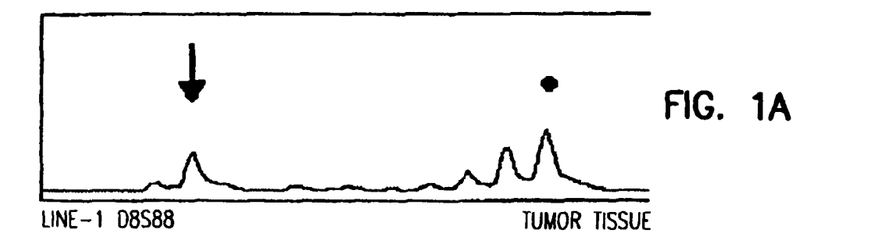
FIG. 1A-1J depicts LOH analysis in microdissected prostate cancer tissues.
Figure 1B:
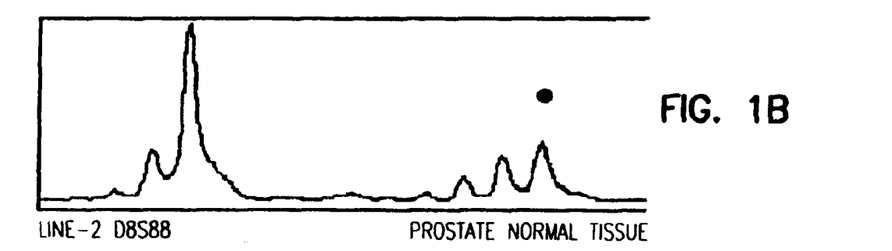
Figure 1C:
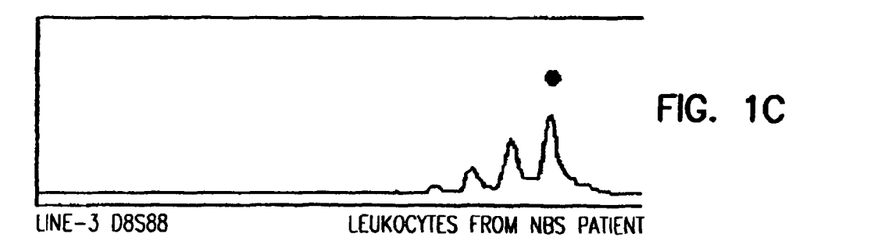
Figure 1D:
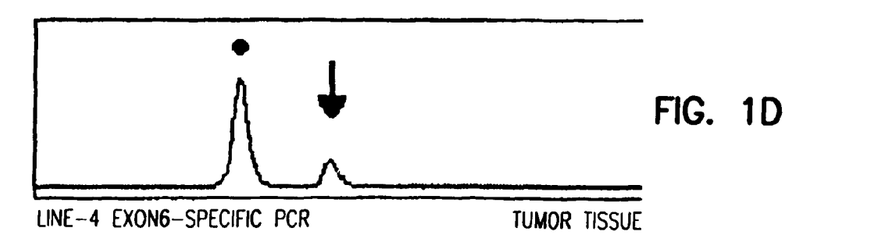
Figure 1E:
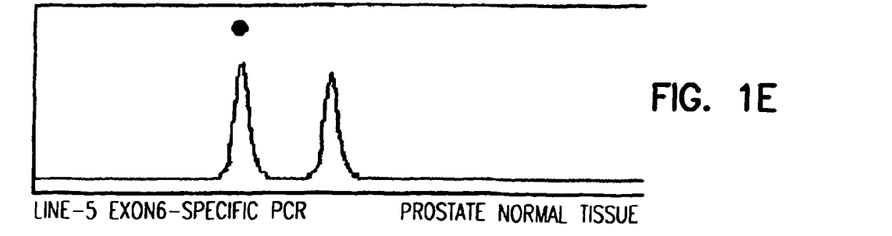
Figure 1F:
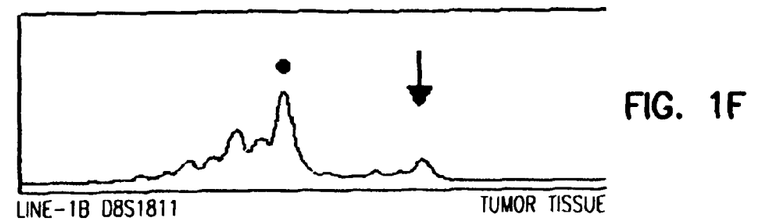
Figure 1G:
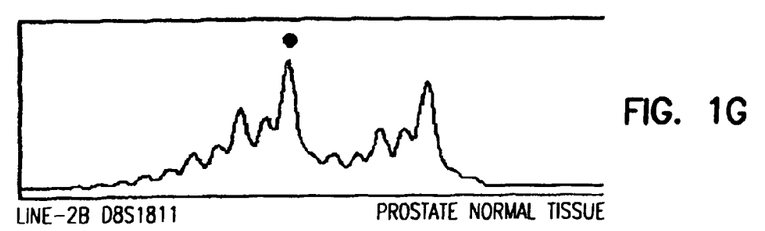
Figure 1H:
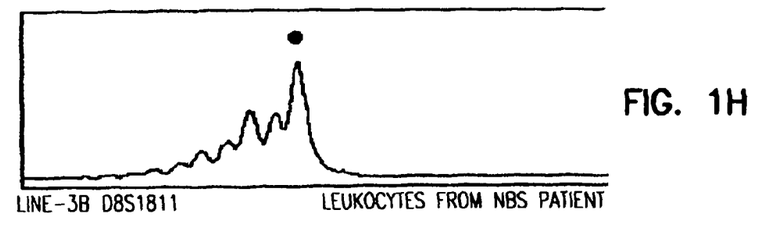
Figure 1I:
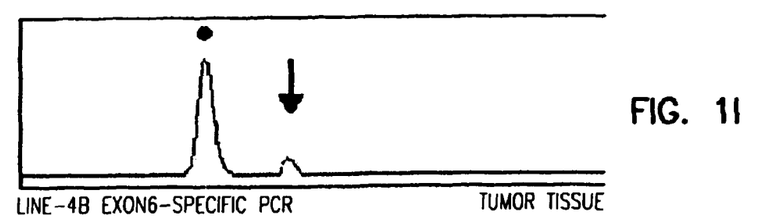
Figure 1J:
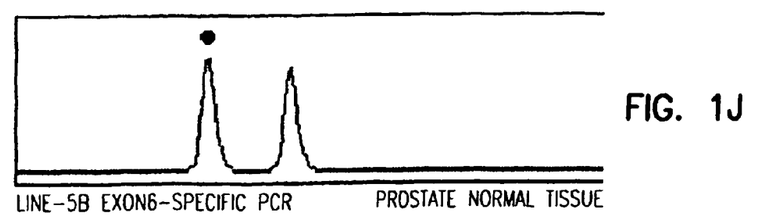

FIG. 1 depicts LOH analysis in microdissected prostate cancer tissues using the markers adjacent to NBS1 gene (lines1-3 and 1b-3b) and using exon6-specific PCR (lines 4-5, 4b-5b). Loss of the wild type allele in cancer tissue is shown by arrows. Dots point at allele with the NBS1 founder mutation.

The NBS1 founder allele appears to be responsible for about one in 11 families with two or more cases of prostate cancer in Poland. Based on a relative risk of 4.5 and a mutadiagnosis of prostate cancer, especially in this ethnic group, may be facilitated by using the simple ASO-PCR assay for the major NBS1 founder mutation. Diagnosis of prostate cancer in other non-Slavic populations may also be similarly facilitated.

The risk for prostate cancer is about 3% in Polish population with 40 million people. Regarding the 2.6% prevalence of NBS1 founder mutation in prostate cancer subjects, about 15 000 NBS1 carriers will develop prostate cancer, that is about 14% of all men affected by the founder NBS1 mutation. As there was a significant difference in prevalence of 657del5 mutation in familial cases compared to consecutive cases (odds ratio=16; 95% CI=5.2 to 50; p<0.0001), prostate cancer risk is higher if a relative of NBS1 carrier is affected by prostate cancer.

This is also the first report showing that NBS1 mutation predisposes to lobular subtype of invasive breast cancer. The risk for invasive lobular breast cancer is about 0.5% in around 20 mln population of Polish women. In regards to the 8% prevalence of NBS1 founder allele in lobular invasive breast cancer subjects, about 8000 NBS1 female carriers will develop breast cancer, that is about 8% of woman with NBS1 founder mutation.

The mean ages of diagnosis of prostate and breast cancers are 68 and 58, respectively. The latter is significantly lower (50 years) for breast cancer diagnosed among NBS1 mutation carriers. Therefore, mammography for NBS1 mutation positive woman should be started earlier, probably not later than at age of 40 years. Thus, protocols for the early detection of breast cancer, distinct from regular standards due to occurrence of NBS1 germline mutation, can be performed.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications cited herein are herein incorporated by reference.

DOCUMENTS CITED

U.S. Pat. No. 6,458,534.
Genbank Accession Number AB013139.
Carney et al., Cell, 93, 477-86 (1998).
Carpten et al., Nat Genet, 30(2), 181-4 (2002).
Cybulski et al., Cancer Research, 64, 1215-1219 (2004).
Dębniak et al., Melanoma Res, 13(4), 365-70 (2003).
Digweed et al., Toxicol. Lett, 67, 259-281 (1993).
Dong et al., Am J Hum Genet, 72(2), 270-80 (2003).
Fan et al., Cancer Gene Ther, 7, 1307-1314 (2000).
Futaki et al., Trends Mol Med, 7, 560-565 (2001).
Gayther et al., Cancer Res, 60, 4513-4518 (2000).
Górski et al., Int J Cancer, 106(3), 379-81 (2003).
Koivisto et al., J Pathol 187, 237-241 (1999).
Lichtenstein et al., N Engl J Med, 343(2), 78-85 (2000).
Matsuura et al., Nat Genet, 19(2), 179-181 (1998).
Plisiecka-HaLasa et al., Ann Hum Genet, 66(Pt 6), 353-9 (2002).
Rebbeck et al., Am J Hum Genet, 67, 1014-1019 (2000).
Seemanova, Mutat Res, 238, 321-4 (1990).
Steffen et al., Frequency of the Heterozygous Germline NBS1 mutation 657del5 in Cancer Patients from Poland. International Workshop on Nijmegen Breakage Syndrome, Prague, Czech Republic 2002.
Tavtigian et al., Nat Genet, 27(2), 172-80 (2001).
van der Burgt et al., J Med Genet, 33, 153-6 (1996).
Varon et al, Cell, 93, 467-76, (1998).
Varon et al., Eur J Hum Genet, 8, 900-902 (2000).
Varon et al., Cancer Res, 61(9), 3570-2 (2001).
Voelkel-Johnson et al., Carcinogenesis 21, 1623-627 (2000).
Wang et al., Cancer Res, 61, 6494-6499 (2001).
Xu et al., Am J Hum Genet, 68, 901-911 (2001).

What is claimed is:

1. A method for detecting a predisposition to breast cancer in a human subject, comprising detecting in a biological sample from the human subject germline alteration 657del5 in the sequence of a NBS1 gene, and associating the alteration with a predisposition to breast cancer in the human subject, thereby detecting the predisposition.

2. The method of claim 1, wherein the breast cancer is invasive breast cancer of the lobular subtype.

3. The method of claim 1, further comprising performing mammography on the subject to detect breast cancer.

4. The method of claim 1, wherein the alteration is present in the sequence of a single allele of the NBS1 gene.

5. The method of claim 1, wherein the alteration is present in the sequence of two alleles of the NBS1 gene.

6. The method of claim 1, wherein the human is of Slavic origin.

7. The method of claim 1, wherein the alteration is detected by microchip, ASO PCR, SSCP, direct sequencing, ASA, or RFLP-PCR.

8. The method of claim 1, wherein the predisposition is an inherited predisposition.

9. The method of claim 1, wherein the biological sample is biological material of any kind.

10. The method of claim 9, wherein the biological sample is blood.

11. The method of claim 1, wherein the biological sample comprises leukocytes.

12. The method of claim 1, wherein the human subject is female.

* * * * *

SEQUENCE LISTING

<160> NUMBER OF SEQ ID NOS: 8

<210> SEQ ID NO 1
<211> LENGTH: 540
<212> TYPE: DNA
<213> ORGANISM: Homo sapiens

<400> SEQUENCE: 1

```
cagataaaat tcttacttaa aaaaaatact ataaaggtat tatggaaatt atgccttttg    60
agtgtcagat agtcactccg tttacaattt aatagcaaac atagtagtat ataattagaa   120
tatactttaa ttatttttac agttttttacc cacctcttga tgaaccatct attggaagta   180
aaaatgttga tctgtcagga cggcaggaaa gaaacaaat cttcaaaggg aaaacattta   240 tattttgaa tgccaaacag gtaattatgt tataagctaa attttcctaa agaatacatt   300
acaaactagg atacattatt aactcttatc agtagttgtt aacgtatttc attttgggat   360
tttgtgtaaa agtgtgaagt agaataaaaa aacccaggc accagacctg cccagtgatc   420
atggctgtga ttacggggtt tcttaaaatc tgtgataact ggcctattca taaatatgca   480
agtgagaagg acaggaaact tagttttaac ttctttagtt agtaagctaa acctctttag   540
```

<210> SEQ ID NO 2
<211> LENGTH: 20
<212> TYPE: DNA
<213> ORGANISM: Homo sapiens

<400> SEQUENCE: 2

```
cacctcttga tgaaccatct                                                 20
```

<210> SEQ ID NO 3

```
-continued

<211> LENGTH: 22
<212> TYPE: DNA
<213> ORGANISM: Homo sapiens

<400> SEQUENCE: 3
cgttaacaac tactgataag ag                                              22

<210> SEQ ID NO 4
<211> LENGTH: 21
<212> TYPE: DNA
<213> ORGANISM: Homo sapiens

<400> SEQUENCE: 4
ggacggcagg aaagaaatct t                                               21

<210> SEQ ID NO 5
<211> LENGTH: 20
<212> TYPE: DNA
<213> ORGANISM: Homo sapiens

<400> SEQUENCE: 5
tccagcagag aaagggttat                                                 20

<210> SEQ ID NO 6
<211> LENGTH: 20
<212> TYPE: DNA
<213> ORGANISM: Homo sapiens

<400> SEQUENCE: 6
ggcaaagaga actcatcaga                                                 20

<210> SEQ ID NO 7
<211> LENGTH: 16
<212> TYPE: DNA
<213> ORGANISM: Homo sapiens

<400> SEQUENCE: 7
cccaccccca aaatgc                                                     16

<210> SEQ ID NO 8
<211> LENGTH: 20
<212> TYPE: DNA
<213> ORGANISM: Homo sapiens

<400> SEQUENCE: 8
gggtttaggg aagtgcagaa                                                 20
```